United States Patent [19]
Lacombe et al.

[11] Patent Number: 6,106,552
[45] Date of Patent: Aug. 22, 2000

[54] CORNEAL PROSTHESIS DEVICE HAVING ANTERIOR AND POSTERIOR ANNULAR SKIRTS

[75] Inventors: Emmanuel Lacombe, Neuilly; Gilles Bos, La Balme de Sillingy; Franck Villain, Annecy, all of France

[73] Assignee: Corneal Industrie, Pringy, France

[21] Appl. No.: 09/117,104

[22] PCT Filed: Jan. 30, 1997

[86] PCT No.: PCT/FR97/00178

§ 371 Date: Jul. 21, 1998

§ 102(e) Date: Jul. 21, 1998

[87] PCT Pub. No.: WO97/27824

PCT Pub. Date: Aug. 7, 1997

[30] Foreign Application Priority Data

Jan. 30, 1996 [FR] France ................................ 96 01066

[51] Int. Cl.⁷ .................................................... A61F 2/14
[52] U.S. Cl. ......................................... 623/5.14; 623/5.13
[58] Field of Search .................................................. 623/5

[56] References Cited

U.S. PATENT DOCUMENTS

| | | |
|---|---|---|
| 2,952,023 | 9/1960 | Rosen . |
| 4,842,599 | 6/1989 | Bronstein . |
| 5,300,115 | 4/1994 | Py . |
| 5,354,332 | 10/1994 | Lacombe . |
| 5,489,301 | 2/1996 | Barber .......................... 623/5 |

FOREIGN PATENT DOCUMENTS

| | | |
|---|---|---|
| 0 469 993 | 2/1992 | European Pat. Off. . |
| 2 649 605 A1 | 1/1991 | France ............................. 623/5 |
| 2687564 | 8/1993 | France . |
| 562277 | 8/1977 | U.S.S.R. ........................... 623/5 |
| 1160623 | 10/1987 | U.S.S.R. ........................... 623/5 |
| 1727823 A1 | 4/1992 | U.S.S.R. ........................... 623/5 |
| WO 89 00032 | 1/1989 | WIPO . |
| WO 93 13731 | 7/1993 | WIPO . |

OTHER PUBLICATIONS

Girard, Advanced Techniques in Ophthalmic Microsurgery, vol. 2, Corneal Surgery, The C.V. Mosby Company, St. Louis, pp. 243–252. 1981.

Polack, Southern Medical Journal, 65 (9), 1118–1122. Sep. 1972.

*Primary Examiner*—David H. Willse
*Attorney, Agent, or Firm*—Wolf, Greenfield & Sacks, P.C.

[57] ABSTRACT

The invention relates to a corneal prosthesis device for putting into place in the cornea. The device comprises an optical part (10) made of a first transparent material and of substantially cylindrical shape presenting an anterior face (14) defining an optical surface and a posterior end (16), an annular anterior skirt (18) projecting from the side wall of the optical part and being made of a biocompatible and biocolonizable synthetic polymer that is distinct from said first material, and a posterior annular skirt (20) projects from the side wall of the optical part and is made of said first material.

19 Claims, 2 Drawing Sheets

CORNEAL PROSTHESIS DEVICE HAVING ANTERIOR AND POSTERIOR ANNULAR SKIRTS

The present invention relates to a corneal prosthesis device.

More precisely, the invention relates to an optical prosthesis which can be put into place by making a central incision in the cornea of the eye when the cornea can no longer perform its function of transparency. Such optical prostheses are sometimes also known as artificial corneas.

Some kinds of blindness are caused by the optical properties of the cornea becoming opaque or spoilt. In some cases, it is possible to remedy that by keratoplasty, i.e. by replacing the unhealthy central portion of the cornea with a fragment of healthy and transparent cornea from a donor. Nevertheless, if the lesions to which the cornea has been subjected are too great (burning, dry syndrome, pseudo-pemphigus), it is necessary to resort to palliative surgery which consists in making an orifice or trephination in the unhealthy portion of the cornea and in putting into place a prosthesis constituting an artificial cornea, with this technique being known as keratoprosthesis.

European patent 0 469 993 describes a corneal prosthesis constituted by an opaque part of substantially cylindrical shape provided at its posterior portion with a support piece secured to the posterior end of the optical part and designed to be pressed against and fixed to the posterior face of the cornea. Various ways of fixing the assembly are envisaged, in particular using an elastic piece disposed at least temporarily at the anterior portion of the corneal prosthesis and/or means for suturing the support piece to the cornea.

This disposition does indeed ensure that the corneal prosthesis can be put into place easily and effectively, and that it is held in the cornea. Unfortunately, it turns out that between the periphery of the prosthesis and the edge of the incision made in the cornea, there is no genuine adherence, thus leaving a path for microbes to the inside of the eye. It will be understood that this situation can be very harmful in certain operations.

An object of the present invention is to provide an improved corneal prosthesis device which is easy to put into place, while nevertheless providing very good sealing between the optical part of the corneal prosthesis and the periphery of the trephination formed in the central portion of the cornea.

According to the invention, to achieve this object, the corneal prosthesis device for putting into place in the cornea and which comprises an optical part made of a first transparent material of substantially cylindrical shape presenting an anterior face defining an optical surface and a posterior end, is characterized in that it further comprises an annular anterior skirt projecting from the side wall of the optical part and made of a biocompatible and biocolonizable synthetic polymer, and a posterior annular skirt projecting from the side wall of the optical part and made of said first material, the distance between the posterior face of the anterior skirt and the anterior face of the posterior skirt is substantially equal to the thickness of the cornea, thereby enabling the cornea to be clamped between the two skirts.

It will be understood that the presence of the annular anterior skirt made of biocolonizable material makes it possible, by various techniques, to cause said anterior skirt to be colonized effectively in such a manner as to provide a sealed discontinuity between the anterior face of the cornea and the optical part of the corneal prosthesis. It should also be understood that the presence of the posterior skirt pressed against the posterior or inside face of the cornea makes it possible to avoid the risk of the prosthesis being expelled under the effect of intraocular pressure.

In a first embodiment, the optical part and the posterior skirt are made of PMMA. In a variant embodiment, the optical part is made of a flexible optical material which may be a silicone gel or a hydrophilic or a non-hydrophilic acrylic.

In a preferred embodiment, the biocolonizable material is selected from those commonly used for reconstructive surgery, and in particular polytetrafluoroethylene and microporous polyethylene.

Other characteristics and advantages of the invention appear better on reading the following description of various embodiments of the invention given as non-limiting examples. The description refers to the accompanying figures, in which.

Figure 1:
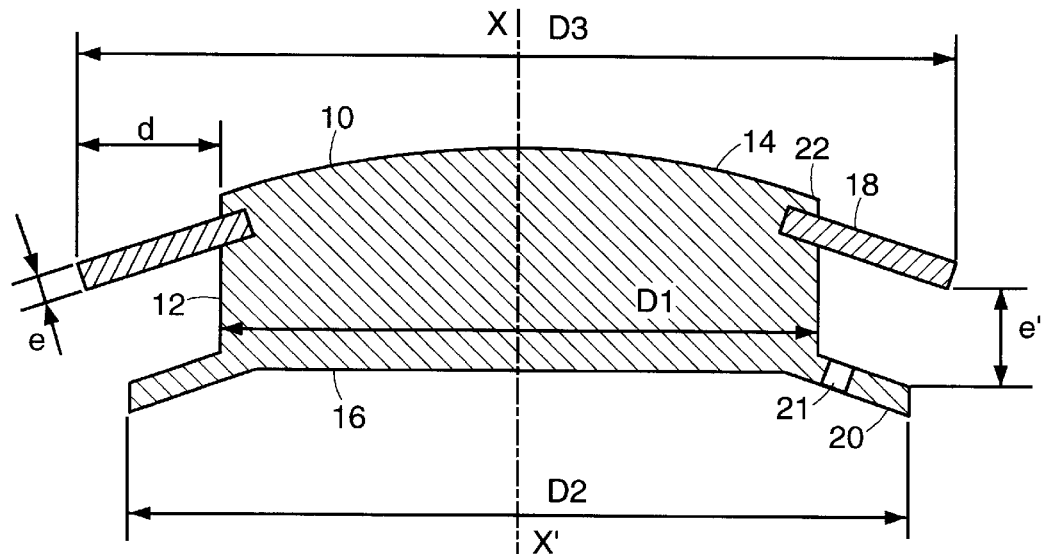
FIG. 1 is a diametral section view through a first embodiment of the corneal prosthesis.

With reference initially to FIG. 1, there follows a description of a first embodiment of the corneal prosthesis device. The device is constituted by an optical part 10 which is of generally cylindrical shape, being symmetrical about the optical axis XX'. The optical part thus includes a substantially cylindrical side wall 12, a front face 14 defining an optical surface for correcting vision, and a rear end 16 which, in this embodiment, constitutes a second optical surface. The corneal prosthesis also includes an anterior skirt 18 fitted thereto which is secured to the side wall 12 of the optical part close to the optical surface 14. The diameter D3 of the anterior skirt is greater than the diameter D1 of the optical part. Finally, the corneal prosthesis includes a posterior skirt 20 which projects from the side wall 12 of the optical part at its posterior end 16. This skirt is preferably slightly frustoconical in shape, extending backwards relative to the posterior face 16. Its diameter is equal to D2. The anterior skirt 18 preferably has the same cone angle as the posterior skirt so that the two skirts are substantially parallel.

In a first embodiment of the corneal prosthesis, the optical part 10 is made of a rigid transparent material such as PMMA. To contribute to holding the anterior skirt 18, the anterior face 14 of the optical part can be extended by an annular rim 22 which partially overlies the anterior face of the anterior skirt. According to an essential characteristic of the invention, the anterior skirt 18 is constituted by a synthetic polymer which is biocompatible and biocolonizable. It is thus a micro-porous material. The biocolonizable material 18 preferably consists in polytetrafluoroethylene or a polyethylene. More preferably, the material constituting the anterior skirt 18 presents pores having a diameter lying in the range 20 microns ($\mu$m) to 100 $\mu$m. The porosity of the material, i.e. its empty space, is preferably greater than 50% of its empty volume. To enable the material to be colonized effectively by living tissue, it is necessary for the "cavities" that result from the porosity of the material to be "open", i.e. they must communicate with one another so as to provide colonization "paths" passing through the skirt from one face to the other to ensure that sufficient colonization takes place and that said colonization by tissue remains "alive". For example, one such material can be obtained by sintering microbeads of different diameters. The term "microporous material" should be understood in this sense.

The diameter D1 of the optical part which provides optical correction thus has a diameter lying in the range 3 mm to 7 mm, and is preferably equal to 5 mm. The thickness e of the anterior skirt 18 preferably lies in the range 10 $\mu$m to 500 $\mu$m, so as to provide sufficient mechanical strength while also ensuring optimum conditions for colonization. More preferably, this thickness lies in the range 50 $\mu$m to 200 $\mu$m. The distance e' between the posterior face of the anterior skirt 18 and the anterior face of the posterior skirt 20 preferably lies in the range 400 $\mu$m to 700 $\mu$m, which corresponds to the thickness of a normal healthy cornea. More generally, to adapt to the various possible thicknesses of cornea, possibly suffering from a pathological condition, the length e' can lie in the range 300 $\mu$m to 2 mm. The thickness of the posterior skirt 20 may lie in the range 100 $\mu$m to 500 $\mu$m, and is typically equal to 250 $\mu$m. To ensure that the corneal prosthesis has good mechanical behavior, the length d by which the anterior skirt projects beyond the side wall of the optical part preferably lies in the range 1 mm to 2 mm, thus leading to a diameter D3 lying in the range 5 mm to 11 mm. The posterior skirt 20 preferably has holes 21 for suturing the prosthesis to the cornea. The diameter D2 can be slightly smaller than D3. Nevertheless, it must be sufficient to prevent the prosthesis being expelled under the effect of ocular pressure, and to leave room for the suturing holes.

Figure 2:
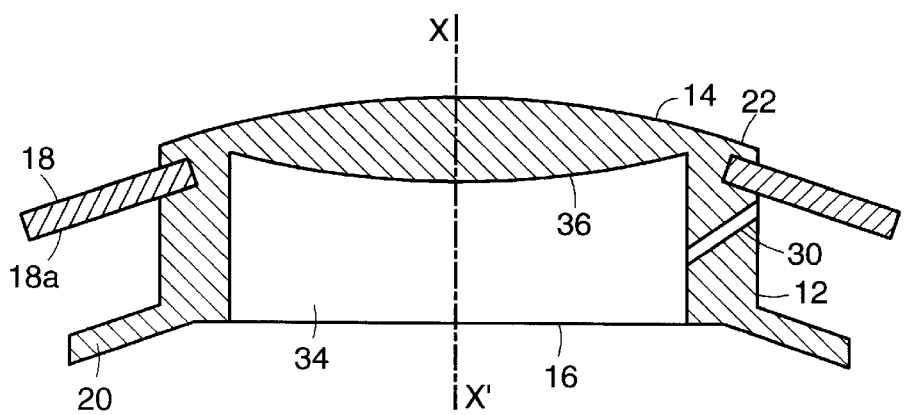
FIG. 2 is a section view on the same plane through a second embodiment of the corneal prosthesis.

In the corneal prosthesis of FIG. 2, the optical part 10 has a substantially cylindrical cavity 34 opening out to the posterior face 16 of the prosthesis, the end wall of the cavity 34 defining an optical surface 36 which may be concave, convex, or plane. The corrective optical system is thus constituted by the portion of the optical part which is defined by the optical surfaces 14 and 36. Such a solution is particularly advantageous when the optical part is not made of a rigid material such as PMMA, but is made using a flexible material as is commonly used for intraocular implants. The flexible material may be a silicone gel or a hydrogel, in particular a hydrophilic acrylic, a good example of which is pHEMA. The fact that the material is flexible and that the optical part is of smaller thickness makes it possible to measure ocular pressure in spite of the presence of the corneal prosthesis. The same material could also be used to make the optical part constituting the embodiment of FIG. 1.

FIG. 2 also shows the possibility of providing a channel 30 of small section passing through a portion of the optical part and putting the cavity 34 of the optical part into communication with the side wall 12 of said optical part close to the posterior face 18a of the anterior skirt 18. This channel of very small section serves to drain the aqueous humor. The presence of this channel makes it possible to combat effectively any increase in intraocular pressure associated with glaucoma. Since the channel opens out behind the anterior skirt 18, the channel is protected from possible invasion by microbes. The small section 30 of the channel can be changed or enlarged by using a laser. It is therefore provided in an initially closed state and is subsequently opened by means of a YAG laser, where necessary.

Naturally, a channel similar to the channel 30 could be provided in the embodiment of FIG. 1. In which case it would put the posterior face 16 into communication with the side wall 12.

Figure 3:
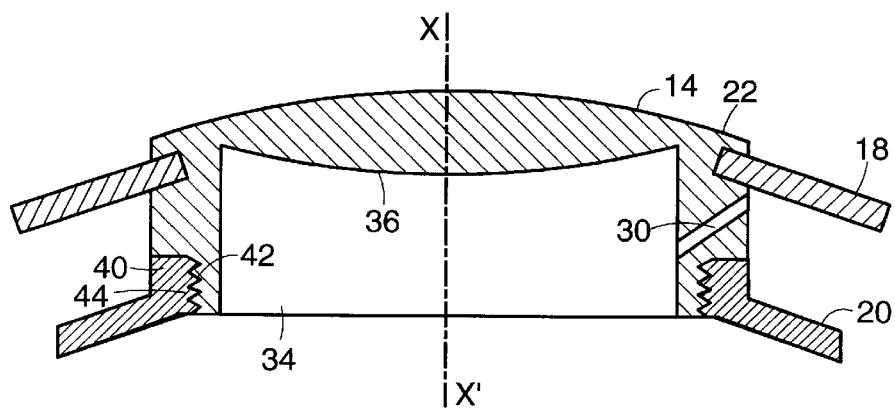
FIG. 3 is a diametral section view of a third embodiment of the corneal prosthesis.

FIG. 3 shows a third embodiment of the corneal prosthesis which differs from the embodiment of FIG. 2 simply by the fact that the posterior skirt 20 is constituted by a part that is separate from the optical part 10. For this purpose, the skirt 20 can be extended by a sleeve 40 fitted with tapping 42. The corresponding portion of the side wall of the optical part is naturally itself provided with a thread 44. It will thus be understood that it remains possible to "dismantle" the corneal prosthesis by unscrewing the optical part from the skirt 20. This ability to dismantle the prosthesis may possibly be used for cleaning the posterior face 16 or 36 thereof, should it become covered in an opaque membrane.

It will be understood that in all embodiments, the fitted anterior skirt made of a biocolonizable material serves both to secure the prosthesis to some extent relative to the cornea, and also, and above all, to provide complete sealing against microbes between the cornea and the prosthesis.

Although tissue constituting a healthy cornea can colonize the microporous material, it is more doubtful whether it can be colonized by unhealthy corneal tissue. It is preferable to obtain colonization by applying healthy tissue of the mouth mucous membrane or conjunctive type.

Naturally, there must be a mechanical connection between the optical part and the anterior skirt 18. This connection may be obtained by placing the anterior skirt in a mold which is used for fabricating the optical part by injection molding, with the anterior skirt acting as an insert. After unmolding, a prosthesis is obtained in which the anterior skirt is secured to the optical part.

It is also possible to provide the mechanical connection by localized and temporary partial melting of the PMMA and of the microporous material. This partial melting can be obtained by ultrasound or by chemical dissolution. In all cases, it is naturally essential to provide between these two parts a sealed connection which presents good mechanical strength.

It will also be understood that the posterior skirt has its anterior face pressed against the posterior or inside face of the cornea. Thus, even under the effect of intraocular pressure, the corneal prosthesis does not run the risk of being expelled from the eye since said pressure tends to press the posterior skirt against the posterior face of the cornea.

Because the thickness of the prosthesis between the two skirts is substantially equal to the thickness of the cornea, biocolonization of the anterior skirt of the prosthesis is facilitated.

Figure 4A:
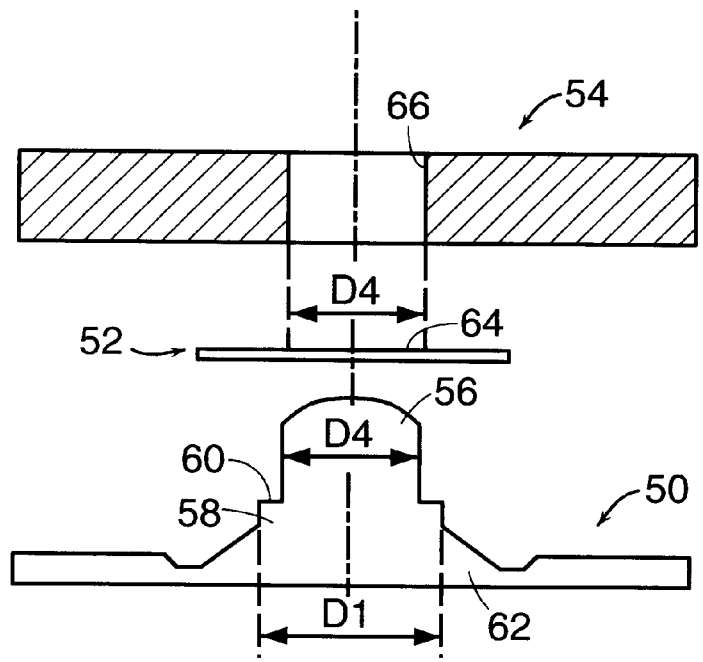
FIGS. 4a and 4b show the steps in a preferred method of fabricating the corneal prosthesis of the invention.
Figure 4B:
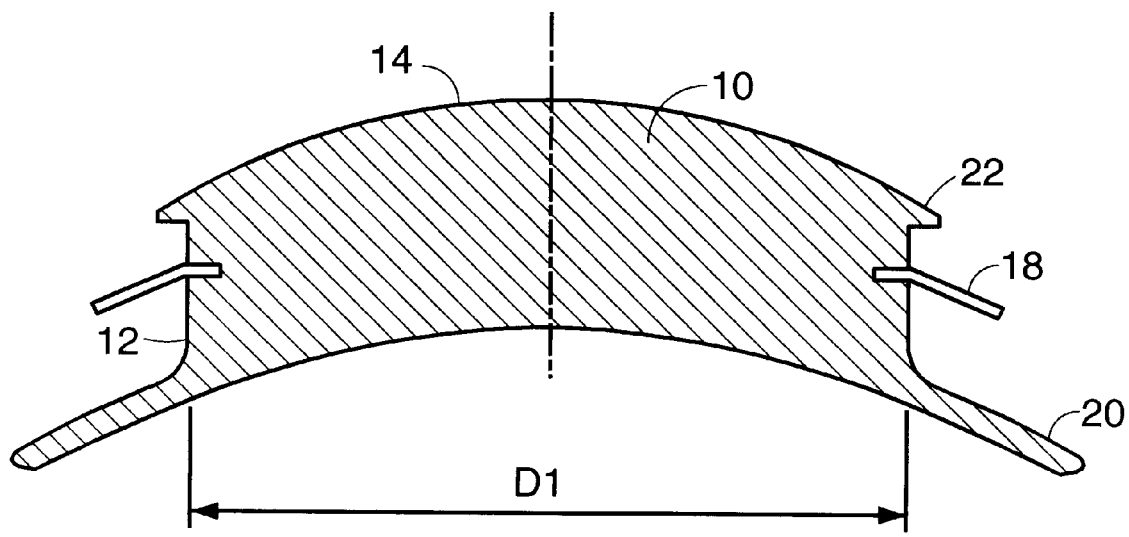

Reference is made below to FIGS. 4a and 4b while describing a preferred but not exclusive method of fabricating the corneal prosthesis of the invention.

In FIG. 4a, there can be seen the three initial parts, namely a blank 50 for the corneal prosthesis, a disk or pellet 52 made using the biocolonizable material, and a ring 54, with the blank 50 and the ring 54 both being made out of the same material which is PMMA, for example. The blank 50 has a central portion 56 including a first cylindrical portion of diameter D4 smaller than the diameter D1 of the optical part of the corneal prosthesis to be made and it is connected to a second substantially cylindrical portion 58 via a shoulder 60. The diameter of the second portion is equal to D1. Finally, the blank has a portion forming a plate 62 from which the posterior skirt is cut out. The pellet 52 is pierced by an axial hole 64 of diameter D4. The same applies to the ring 54 which has an axial orifice 66 of diameter D4.

The pellet 52 is placed on the shoulder 58 and then the ring 54 is placed on the pellet 52, the cylindrical portion 56 of the blank being engaged in the axial holes through these two parts.

Heat is then applied, e.g. by ultrasound, thereby welding the ring 54 to the cylindrical portion 56 of the blank 50. The pellet 52 of biocolonizable material is then held captive between the shoulder 58 and the ring 54.

Finally, the blank 50 and the ring 54 are machined to give the final shape to the optical part of the corneal prosthesis and to its posterior skirt. FIG. 4b shows the corneal prosthesis obtained after the blank and the ring has been machined appropriately.

What is claimed is:

1. A corneal prosthesis device for being placed in a hole of a cornea of an eye, the cornea having a thickness and a posterior face, the device comprising:

an optical part made of a first transparent material, the optical part being of substantially cylindrical shape and having an anterior face defining an optical surface and a posterior face and a side wall;

an annular anterior skirt disposed close to said anterior face and projecting from said side wall of the optical part and being made of a biocompatible and biocolonizable synthetic polymer distinct from said first transparent material; and a posterior annular skirt disposed close to said posterior face and projecting from said side wall of the optical part, said posterior skirt being secured to said optical part and having a fixed position with respect to said optical part, said posterior skirt being secured prior to placement of the corneal prosthesis device in the eye and having a fixed distance between the anterior and posterior skirts substantially equal to the thickness of the cornea.

2. The corneal prosthesis device according to claim 1, wherein the anterior face of the optical part defines a rim which partially overlies an anterior face of the anterior skirt.

3. The corneal prosthesis device according to claim 1, wherein said optical part includes a recess whose end wall defines a second optical surface.

4. The corneal prosthesis device according to claim 1, wherein said optical part includes at least one small section channel having a first end opening out into the posterior face of the optical part and having its second end opening out in the side wall thereof close to a posterior face of said anterior skirt.

5. The corneal prosthesis according to claim 1, wherein said posterior skirt is a part that is distinct from the optical part, said posterior skirt being screwed to a posterior end of the optical part prior to placement of the corneal prosthesis in the eye.

6. The corneal prosthesis device according to claim 1, wherein said optical part is made of acrylic.

7. The corneal prosthesis device according to claim 6, wherein said optical part is made of PMMA.

8. The corneal prosthesis device according to claim 1, wherein said optical part is made of a flexible material selected from the group comprising silicone gels and acrylics.

9. The corneal prosthesis device according to claim 1, wherein said biocolonizable synthetic polymer has pores of a diameter lying in the range 20 $\mu$m to 100 $\mu$m, with the empty volume representing at least 50% of the total volume.

10. The corneal prosthesis device according to claim 1, wherein said biocolonizable synthetic polymer is selected from the materials used in reconstructive surgery.

11. The corneal prosthesis device according to claim 9, comprised of polytetrafluoroethylene or of polyethylene.

12. The corneal prosthesis device according to claim 1, wherein an outside diameter of the anterior skirt lies in the range of from 5 mm to 11 mm.

13. The corneal prosthesis device according to claim 1, wherein a thickness of the anterior skirt lies in the range of from 20 $\mu$m to 500 $\mu$m.

14. The corneal prosthesis device according to claim 1, wherein a diameter of the optical part lies in the range of from 3 mm to 7 mm.

15. The corneal device according to claim 1, wherein said anterior and posterior skirts are substantially parallel to each other.

16. The corneal prosthesis device according to claim 1, wherein the fixed distance between the two skirts lies in the range of from 400 $\mu$m to 700 $\mu$m.

17. The corneal prosthesis device according to claim 1, wherein said posterior skirt is adapted to contact the posterior face of the cornea such that pressure of liquid within the eye holds said posterior skirt in place against said posterior face of said cornea.

18. The corneal prosthesis device according to claim 1, wherein said posterior skirt is fixably secured to said optical part prior to placement of the corneal prosthesis device in the eye.

19. The corneal prosthesis device according to claim 1, wherein the posterior skirt is formed from the first transparent material.

* * * * *